United States Patent [19]
Carter et al.

[11] Patent Number: 6,081,743
[45] Date of Patent: *Jun. 27, 2000

[54] METHOD AND APPARATUS FOR TREATING AN INDIVIDUAL USING ELECTROENCEPHALOGRAPHIC AND CEREBRAL BLOOD FLOW FEEDBACK

[76] Inventors: John Leland Carter, 15506 Penn Hills, Houston, Tex. 77062; Harold Laverne Russell, P.O. Box 240; W. Daniel Vaughn, P.O. Box 629, both of Galveston, Tex. 77553; Robert Raoul Austin, P.O. Box 95530, Seattle, Wash. 98145

[*] Notice: This patent issued on a continued prosecution application filed under 37 CFR 1.53(d), and is subject to the twenty year patent term provisions of 35 U.S.C. 154(a)(2).

[21] Appl. No.: 08/725,115

[22] Filed: Oct. 2, 1996

[51] Int. Cl.$^7$ .................................................. A61B 5/04
[52] U.S. Cl. ........................ 600/544; 600/504; 600/545
[58] Field of Search .................................. 600/544, 545, 600/483, 504

[56] References Cited

U.S. PATENT DOCUMENTS

| | | | |
|---|---|---|---|
| 4,862,359 | 8/1989 | Trivedi et al. | 600/544 |
| 5,036,858 | 8/1991 | Carter et al. | 600/545 |
| 5,230,344 | 7/1993 | Ozdamar et al. | 600/544 |
| 5,309,923 | 5/1994 | Leuchter et al. | 600/544 |
| 5,331,969 | 7/1994 | Silberstein | 600/544 |
| 5,365,939 | 11/1994 | Ochs | 600/544 |
| 5,402,797 | 4/1995 | Akiyama et al. | 600/545 |
| 5,495,853 | 3/1996 | Yasushi | 600/545 |
| 5,584,297 | 12/1996 | Bodo et al. | 600/483 |
| 5,699,808 | 12/1997 | John | 600/483 |

*Primary Examiner*—Max Hindenburg
*Assistant Examiner*—Charles Marmor, II
*Attorney, Agent, or Firm*—Timmons & Kelly; W. Thomas Timmons

[57] ABSTRACT

A method for treating an individual includes selecting a reference site or sites for determining a brain wave frequency of the individual, determining an initial brain wave frequency of the individual, determining a brain wave frequency which corresponds to a highest evoked response of the individual, by use of electroencephalographic (EEG) feedback, entraining the brain wave frequency of the individual at the chosen site or sites to the brain wave frequency corresponding to the highest evoked response, and then maintaining the brain wave at that frequency for a first predetermined length of time. The highest evoked response can be the highest EEG response or the highest cerebral blood flow (CBF) of the individual or even some other measure. The CBF can be either for a selected portion of or the entire cerebrum. In one embodiment, the method includes repeating some steps. A preferred method entrains the individual back to approximately the initial brain wave frequency of the individual. An apparatus according to the present invention includes a computer processor, a device for determining a current brain wave frequency of an individual and a device for producing an output detectable by the individual.

20 Claims, 2 Drawing Sheets

METHOD AND APPARATUS FOR TREATING AN INDIVIDUAL USING ELECTROENCEPHALOGRAPHIC AND CEREBRAL BLOOD FLOW FEEDBACK

BACKGROUND OF THE INVENTION

1. Field of the Invention

The present invention relates generally to methods and apparatus for controlling brain wave frequencies and cerebral blood flow and to therapeutic uses of such methods and apparatus.

Human brains disturbed by social, mechanical, chemical or other trauma become both restricted in their electrical and chemical activity and hypersensitive to internal and external events and stimuli. In one of its aspects, the present invention pertains to the assessment and amelioration of functioning after psychological and mechanical trauma, or the enhancement of typical brain functioning, through the disruption of the restriction and rigidity of neural activity.

2. Description of Related Art

In the 1960's and early 1970's, Robert Monroe of the Monroe Institute of Applied Sciences explored the effects of sound on the brain and discovered that he could produce a driving or entrainment of brain waves. Dr. Gerald Oster, a biophysicist, also investigating the effects of sound on the brain, discovered that pulsations called binaural beats occurred in the brain when tones of different frequencies were presented separately to each ear. The beat frequency equals the frequency difference between the two tones. Both Monroe and Oster began using electronic oscillators to provide tones with frequency, purity and intensity that can be precisely controlled.

U.S. Pat. No. 3,884,218 to Robert A. Monroe shows a method for inducing sleep by amplitude modulating a pleasing sound with a delta-rhythm signal which is referred to as an "EEG sleep signal."

U.S. Pat. No. 4,191,175 to Nagle shows a method and apparatus for repetitively "producing a noise-like signal for inducing a hypnotic or anesthetic effect . . . " by creating frequency bursts of digital pulses that are then passed through a pink noise filter to get rid of frequencies above a certain cut-off. The resultant signal is then passed through a band pass filter and used to drive an audible signal source.

An apparatus for electrophysiological stimulation is shown in U.S. Pat. No. 4,227,516 to Meland et al. in which a first signal above the delta-beta frequency range is modulated by signal within that range and applied to electrodes on the forehead of a user.

A learning-relaxation device of U.S. Pat. No. 4,315,502 has both lights for pulsing signals and sound means for a pulsing sound signal as well as a control means which can individually vary the light and sound signals.

U.S. Pat. No. 4,834,701 to Masaki shows a device similar to those used by Monroe and Oster with first and second generators with frequencies above 16 hertz and a frequency difference of 4 to 16 hertz sounded to lower the brain wave frequency of a user. The term "entrainment" began to be accepted for such devices: "This phenomenon, in which one regular cycle locks into another, is now called entrainment, or mode locking." (Gleick, Chaos: Making of a New Science 1987, Penguin Books, p. 293). An article entitled "Alpha Brain Waves & Biofeedback Training" in the December 1972 *Popular Electronics* show a system that uses a person's own EEG signal to modulate a tone generator which, in turn, then drives a speaker heard by the same person. The device allowed a person to "hear" his or her own brain signals in an attempt to voluntarily control the frequency. A similar device that allows a person to "see" his or her own brain waves is shown in an article entitled "Mind Power: Alpha" in the July 1976 *Radio-Electronics*.

U.S. Pat. No. 5,036,858 to John L. Carter, Harold L. Russell and Len Ochs shows the use of EEG electrodes attached to the head of the user along with an amplifier for determining a current brain wave frequency of a user, which is communicated to a computer processor. A new frequency is generated which is between the current brain wave frequency and a desired brain wave frequency and is within a predetermined range of the current brain wave frequency. This has become known as electroencephalographic entrainment feedback if it is used to "lock" the current brain wave frequency into a desired frequency.

U.S. Pat. No. 5,365,939 to Len Ochs provides a method of "exercising" the brain by using a device producing audio and visual stimulation to move a user's brain wave frequency back and forth between predetermined frequency levels.

Prior methods for assessment of neural function involve radiographic, magnetic, electrical and nuclear evaluations with eyes open or eyes closed states, or at best, the neuronal or other activity evoked under different conditions such as reading, drawing, doing arithmetic, etc. Static frequency stimulation, even that steady frequency stimulation which alternates from time to time, is used to assess the presence and kind of seizure activity.

Methods of treatment have in many ways attempted to ameliorate brain functioning by either providing the brain with a faithful and accurate picture of its activity, or with a means of targeting a desired frequency, range of frequencies, or relationship among frequencies, or have targeted theoretically and empirically derived frequency states as a goal of training or therapy. Methods using feedback have largely involved conscious, voluntary processes in the amelioration of neural functioning. Such methods have not fitted the stimulation frequencies to real-time measurements of neural frequency. They have taken as a goal to feedback to the brain information as to success at reaching target neural activity. These methods require conscious attention, concentration, analysis and learning.

SUMMARY OF THE INVENTION

A method for treating an individual according to the present invention includes the steps of selecting a reference site or sites for determining a brain wave frequency of the individual, determining an initial brain wave frequency of the individual, determining a brain wave frequency which corresponds to a highest evoked response of the individual, by use of electroencephalographic (EEG) feedback, entraining the brain wave frequency of the individual at the chosen site or sites to the brain wave frequency corresponding to the highest evoked response, and then maintaining the brain wave frequency of the individual at substantially the frequency corresponding to the highest evoked response for a first predetermined length of time. The highest evoked response can be the highest EEG response or the highest cerebral blood flow (CBF) of the individual or even some other measure. The blood flow can be either for a selected portion of the cerebrum, known as regional cerebral blood flow (RCBF), or the entire cerebrum, CBF. The step of determining the frequency of highest evoked response would include EEG entrainment over a range of interest, possibly from as low as 2 to as high as 30, determining the response as a function of frequency. During this time, and throughout the entire treatment, certain brain wave markers should be watched for, such as a marker for seizure activity or migraine headache. Should such a marker be detected, then the procedure would be terminated or the individual would be immediately entrained back to the initial brain wave frequency or some other suitable emergency procedure would be followed.

In one embodiment, the method includes repeating the steps of determining a brain wave frequency which corresponds to a highest evoked response of the individual, by use of EEG feedback, entraining the brain wave frequency of the individual at the chosen site to the brain wave frequency corresponding to the highest evoked response, and maintaining the brain wave frequency of the individual at substantially the frequency corresponding to the highest evoked response for a first predetermined length of time. The session can be ended at this point, or an alternative method for treating an individual according to the present invention also includes the step, following the expiration of the first predetermined length of time, by means of EEG feedback, of entraining the brain wave frequency of the individual back to approximately the initial brain wave frequency of the individual.

A preferred form of an apparatus according to the present invention for urging the brain wave frequency of an individual toward a desired frequency and for maintaining a desired frequency includes a computer processor, a memory which can be written to and read from the computer processor, a computer program within the memory, means such as EEG electrodes attached to the head of the individual for determining a current brain wave frequency of an individual, which means communicates through an amplifier with the computer processor, a programmable timing generator responsive to the computer processor, generating at least a first and a second signal, and means detectable by the individual for producing an output corresponding to the first and second signals. The frequency difference between the first and second signals is between the current brain wave frequency and the desired brain wave frequency and is within a predetermined range of the current brain wave frequency. In one preferred arrangement, a radiation detection device is used to determine the amount of radiotracer in a selected portion of the individual's cerebrum, which information is fed into the computer processor to determine the amount of CBF with respect to brain wave frequency.

In one arrangement, an option is given to determine a limiting frequency which may be a target brain wave frequency or a limit on the range of possible frequencies.

These and other objects, advantages and features of this invention will be apparent from the following description taken with reference to the accompanying drawing, wherein is shown a preferred embodiment of the invention.

DESCRIPTION OF THE PREFERRED EMBODIMENT

Figure 1:
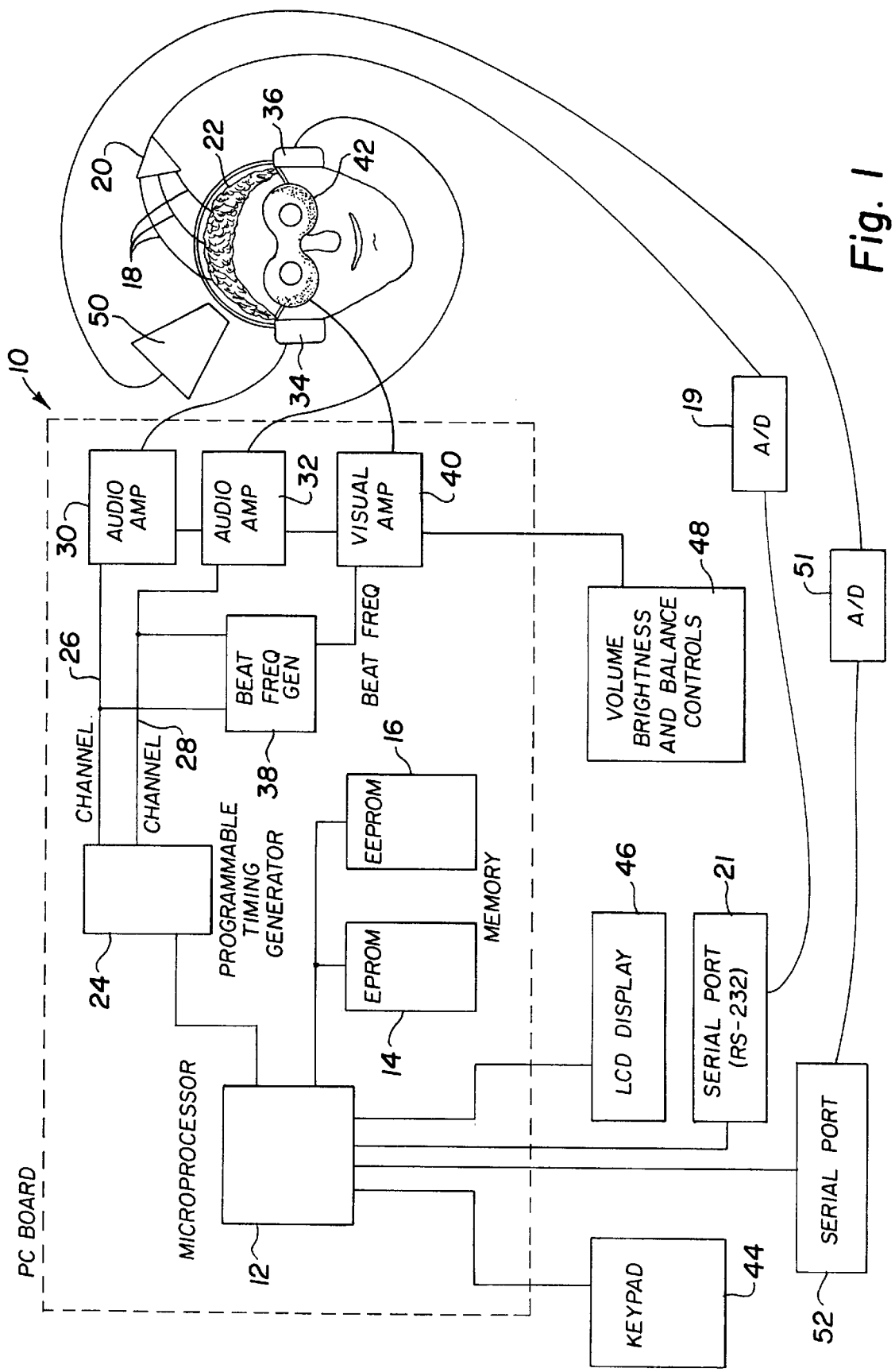
FIG. 1 is a block diagram representation of an apparatus suitable for the method of the current invention.

Referring now to the drawing, and in particular to FIG. 1, an apparatus for practicing a method according to the present invention is represented generally by reference numeral 10 and would be similar to that shown in the Carter/Russell patent. Apparatus 10, which can include a general purpose computer such as any number of personal computers or a special purpose apparatus, includes a computer processor such as microprocessor 12, memory 14 and 16 which can be written to or read from the microprocessor for storing programs and data, and means such as electrodes 18 and amplifier 20 for determining a current brain wave of an individual, user 22. Electrodes 18 are placed at selected sites on the user's head for determining the user's brain wave frequency. The brain wave frequency can be determined by averaging the frequency at the different sites or any two of the sites, known as bipolar, or by selecting one of the sites, known as monopolar. Electrodes 18 and amplifier 20 communicate with microprocessor 12 through serial port 21 after being converted to digital form by analog-to-digital converter 19. A programmable timing generator 24 is responsive to microprocessor 12 and generates a first signal at a first frequency on a first channel 26 and a second signal at a second frequency on a second channel 28. The frequency difference between the first and second signals is between the current brain wave frequency and the desired brain wave frequency and is within a predetermined range of the current brain wave frequency. First audio amplifier 30 along with right earphone 34 sounds the first signal to the right ear of the individual, and second audio amplifier 32 along with left earphone 36 sounds the second signal to the left ear of the individual.

The first and second signals are combined in beat frequency generator 38. The combined signal is then amplified by visual amplifier 40, yielding a beat signal equal to the frequency difference which is used to drive light goggles 42. The light or strobe frequency could, of course, be generated directly. Facilities are also available to supply a different frequency to each eye, which might also have applicability in the present invention.

Keyboard 44 and display 46, which can be a conventional computer monitor or a special purpose liquid crystal or other type display, together with Microprocessor 12 and memory 14 and 16 could form part of a personal or even a lap-top computer. Volume, brightness and balance controls 48 are used to adjust to the individual user 22 and the purpose of the use. They could be controlled through the computer rather than directly as shown.

In one arrangement, user 22 has a radioactive tracer, also known as a radiotracer, injected into his or her blood. Radiation detection device 50 detects the amount of radiotracer in a targeted portion of the individual's cerebrum. The information gathered by radiation detection device 50 is fed to microprocessor 12 by means of serial port 52 after being converted into digital form by analog-to-digital converter 51. In the microprocessor, or other computer, the information gathered from radiation detection device 50 is processed by a single-photon emission computed tomography (SPECT) to yield RCBF for the targeted portion of the individual's cerebrum. The targeted portion could, of course, be the entire cerebrum. An alternative way of determining relative cerebral blood flow is to measure scalp temperature by means of a rheoencephalograph.

Figure 2:
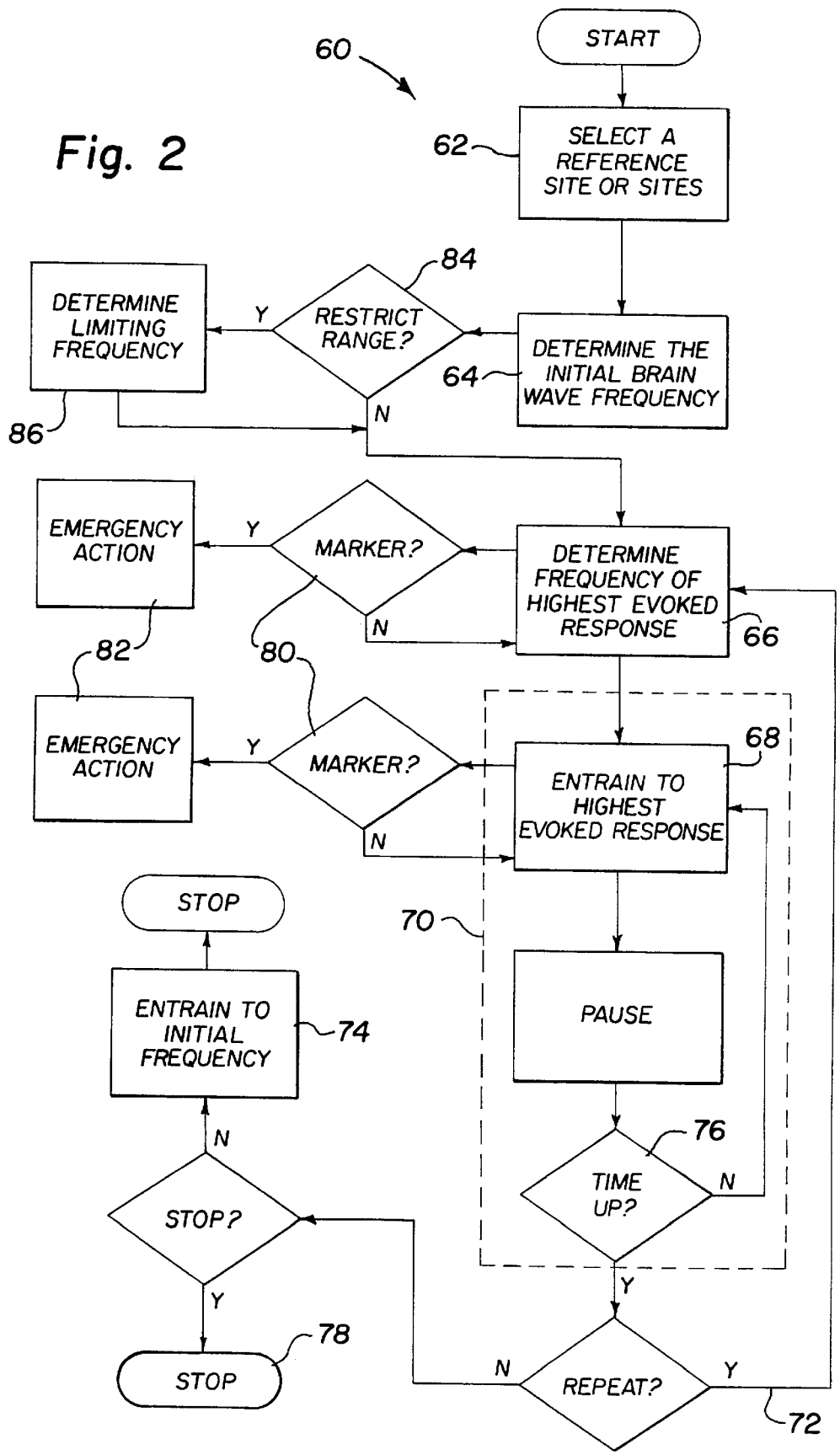
FIG. 2 is a flow diagram representation of an overall method according to the present invention.

Referring now to FIG. 2, an overall method according to the present invention for treating an individual, referred to by reference numeral 60, includes step 62 of selecting a reference site or sites for determining a brain wave frequency of the individual, determining 64 an initial brain wave frequency of the individual, determining 66 a brain wave frequency which corresponds to a highest evoked response of the individual, by use of electroencephalographic (EEG) feedback, entraining 68 the brain wave frequency of the individual at the chosen site or sites to the brain wave frequency corresponding to the highest evoked response, and then maintaining 70 the brain wave frequency of the individual at substantially the frequency corresponding to the highest evoked response for a first predetermined length of time 76. In one arrangement, the step 70 of maintaining the selected brain wave frequency can include the step 76 of pausing for a predetermined length of time, i.e. not producing detectable signals for entrainment. The detectable signals can then be resumed, creating cycles of periodic pauses and active times. The highest evoked response can be the highest EEG response or the highest CBF or RCBF of the individual or even some other measure such as the product of frequency times CBF. For some individuals, increased blood flow occurs after a few seconds, while for other individuals, the increased blood flow may not be for as long as fifteen minutes after the initial stimulus. Because of such wide variability, the determination of the frequency of highest evoked CBF or RCBF needs to be flexible.

In one embodiment, the method includes repeating 72 the steps of determining 66 a brain wave frequency which corresponds to a highest evoked response of the individual, by use of EEG feedback, entraining 68 the brain wave frequency of the individual at the chosen site or sites to the brain wave frequency corresponding to the highest evoked response, and maintaining 70 the brain wave frequency of the individual at substantially the frequency corresponding to the highest evoked response for a first predetermined length of time.

One method for treating an individual according to the present invention also includes the step, following the expiration of the first predetermined length of time, by means of EEG feedback, of entraining 74 the brain wave frequency of the individual back to approximately the initial brain wave frequency of the individual. An alternative is the step 78 of stopping the procedure while the user 22 is still at the selected brain wave frequency.

In one alternative procedure according to the present invention, an option 84 is given to determine 86 a limiting frequency which may be a target brain wave frequency or a limit on the range of possible frequencies. If such an option is chosen, then the other steps in the procedure would operate with that limit. The range of possible brain wave frequencies may be limited if it is known that user 22 is prone to seizures above the limiting frequency. A target frequency may be chosen where increased CBF is normally expected if user 22 appears to not be responding to normal changes in frequency or where the user's highest response is already known.

Throughout the procedure, user 22 is monitored 80 to determine if any markers are present in the brain wave pattern which would indicate a problem or if there are other signs of distress. As used herein, the term "marker" means any electro-physiological or neurophysiological changes detected by the EEG monitor which may be a precursor to seizure or migraine activity or lowering the seizure or migraine threshold. If such a marker is present, then emergency action 82 is taken. Such emergency action could be completely shutting down or removing visual stimulation or returning the user to the initial brain wave frequency or possibly taking medical action, depending on the particular marker or distress sign. In a preferred form, the computer is programmed to watch for such markers.

It is now clear that if the desired frequency is the frequency of maximum evoked response, then the brain is entrained to that frequency. Once it reaches that frequency, and the difference between the current frequency and the desired frequency becomes zero, the means for producing an output simply maintains the desired frequency. Maintaining the desired brain wave frequency using periodic pauses would, of course, allow the possibility of a certain decay cycle where the brain wave frequency of the user tends to drift back to some other frequency, but is brought back to the desired frequency during the active part of the cycle.

From the foregoing it will be seen that this invention is well adapted to attain all of the ends and objectives hereinabove set forth, together with other advantages which are inherent to the apparatus.

It will be understood that certain features and sub combinations are of utility and may be employed without reference to other features and sub combinations. This is contemplated by and is within the scope of the claims.

As many possible embodiments may be made of the invention without departing from the scope thereof, it is to be understood that all matter herein set forth or shown in the figures of the accompanying drawings is to be interpreted as illustrative and not in a limiting sense.

We claim:

1. A method for treating an individual, comprising in combination the steps of:
    determining an initial brain wave frequency of the individual;
    determining a brain wave frequency which corresponds to a highest evoked response of the individual;
    by use of electroencephalographic feedback, entraining the brain wave frequency of the individual to the brain wave frequency corresponding to the highest evoked response; and
    maintaining the brain wave frequency of the individual at substantially the frequency corresponding to the highest evoked response for a first predetermined length of time.

2. A method for treating an individual according to claim 1 wherein the step of determining a brain wave frequency which corresponds to a highest evoked response of the individual comprises determining the highest evoked electroencephalographic amplitude response.

3. A method for treating an individual according to claim 2 further including the step, following the expiration of the first predetermined length of time, by means of electroencephalographic feedback, of entraining the brain wave frequency of the individual back to approximately the initial brain wave frequency of the individual.

4. A method for treating an individual according to claim 1 wherein the step of determining a brain wave frequency which corresponds to a highest evoked response of the individual comprises determining the highest evoked cerebral blood flow response.

5. A method for treating an individual according to claim 4 further including the step, following the expiration of the first predetermined length of time, by means of electroencephalographic feedback, of entraining the brain wave frequency of the individual back to approximately the initial brain wave frequency of the individual.

6. A method for treating an individual according to claim 1 further comprising, following the expiration of the first predetermined length of time, repeating the following sequence of steps at least once:
    determining a brain wave frequency which corresponds to a highest evoked response of the individual;
    by use of electroencephalographic feedback, entraining the brain wave frequency of the individual to the brain wave frequency corresponding to the highest evoked response; and maintaining the brain wave frequency of the individual at substantially the frequency corresponding to the highest evoked response for a first predetermined length of time.

7. A method for treating an individual according to claim 6 wherein each step of determining a brain wave frequency which corresponds to a highest evoked response of the individual comprises determining the highest evoked electroencephalographic amplitude response.

8. A method for treating an individual according to claim 7 further including the step, following the expiration of the first predetermined length of time, by means of electroencephalographic feedback, of entraining the brain wave frequency of the individual back to approximately the initial brain wave frequency of the individual.

9. A method for treating an individual according to claim 6 wherein each step of determining a brain wave frequency which corresponds to a highest evoked response of the individual comprises determining the highest evoked cerebral blood flow response.

10. A method for treating an individual according to claim 9 further including the step, following the expiration of the first predetermined length of time, by means of electroencephalographic feedback, of entraining the brain wave frequency of the individual back to approximately the initial brain wave frequency of the individual.

11. A method for treating an individual according to claim 1 wherein the step of maintaining the brain wave frequency of the individual at substantially the frequency corresponding to the highest evoked response for a first predetermined length of time comprises the steps of:

producing an output detectable by the individual at approximately the frequency corresponding to the highest evoked response;

then producing no output; and then again producing an output detectable by the individual at approximately the frequency corresponding to the highest evoked response.

12. A method for treating an individual according to claim 11 wherein each step of determining a brain wave frequency which corresponds to a highest evoked response of the individual comprises determining the highest evoked electroencephalographic amplitude response.

13. A method for treating an individual according to claim 12 further including the step, following the expiration of the first predetermined length of time, by means of electroencephalographic feedback, of entraining the brain wave frequency of the individual back to approximately the initial brain wave frequency of the individual.

14. A method for treating an individual according to claim 11 wherein each step of determining a brain wave frequency which corresponds to a highest evoked response of the individual comprises determining the highest evoked cerebral blood flow response.

15. A method for treating an individual according to claim 14 further including the step, following the expiration of the first predetermined length of time, by means of electroencephalographic feedback, of entraining the brain wave frequency of the individual back to approximately the initial brain wave frequency of the individual.

16. An apparatus for urging the brain wave frequency of a user toward a desired brain wave frequency, the apparatus comprising in combination:

a computer processor;

means for determining a current brain wave frequency of the user, which communicates with the computer processor;

means for determining cerebral blood flow of the individual, which communicates with the computer processor;

means responsive to the computer processor and detectable by the user for producing an output with a frequency between the current brain wave frequency and the desired brain wave frequency and is within a predetermined range of the current brain wave frequency, wherein the computer processor determines the cerebral blood flow of the individual as a function of frequency.

17. An apparatus according to claim 16 wherein the desired brain wave frequency is the frequency at which cerebral blood flow is greatest.

18. An apparatus according to claim 17 wherein the current brain wave frequency is also the frequency at which cerebral blood flow is greatest and the means for producing an output, produces an output at that frequency.

19. An apparatus according to claim 16 wherein the current brain wave frequency is also the desired brain wave frequency and the means for producing an output, produces an output at that frequency.

20. A method for treating an individual, comprising in combination the steps of:

determining an initial brain wave frequency of the individual;

selecting a limiting brain wave frequency;

determining a brain wave frequency which corresponds to a highest evoked response of the individual in the range between the initial brain wave frequency and the limiting brain wave frequency;

by use of electroencephalographic feedback, entraining the brain wave frequency of the individual to the brain wave frequency corresponding to the highest evoked response in the range; and maintaining the brain wave frequency of the individual at substantially the frequency corresponding to the highest evoked response in the range for a first predetermined length of time.

* * * * *